United States Patent [19]

O'Doherty

[11] 4,011,341
[45] Mar. 8, 1977

[54] RING-SUBSTITUTED N-(2,2-DIFLUOROALKANOYL)-O-PHENYLENEDIAMINE INSECTICIDES

[75] Inventor: George O. P. O'Doherty, Greenfield, Ind.

[73] Assignee: Eli Lilly and Company, Indianapolis, Ind.

[22] Filed: June 25, 1975

[21] Appl. No.: 590,226

Related U.S. Application Data

[60] Division of Ser. No. 479,073, June 13, 1974, Pat. No. 3,907,892, which is a continuation-in-part of Ser. No. 277,452, Aug. 2, 1972, abandoned, which is a continuation-in-part of Ser. No. 47,857, June 19, 1970, abandoned, and a continuation-in-part of Ser. No. 17,865, March 9, 1970, abandoned, which is a continuation-in-part of Ser. No. 803,998, March 3, 1969, abandoned.

[52] U.S. Cl. .................................. 424/324; 424/285
[51] Int. Cl.² ........................ A01N 9/20; A01N 9/24
[58] Field of Search .................... 424/324, 330, 285

[56] References Cited

UNITED STATES PATENTS 3,557,211  1/1971  Rumanowski ..................... 424/324

*Primary Examiner*—V. D. Turner
*Attorney, Agent, or Firm*—Kathleen R. S. Page; Everet F. Smith

[57] ABSTRACT

Ring-substituted N-(2,2-difluoroalkanoyl)-o-phenylenediamine compounds useful as herbicides and as insecticides; and combinations of these compounds with known herbicides.

3 Claims, No Drawings

RING-SUBSTITUTED N-(2,2-DIFLUOROALKANOYL)-O-PHENYLENEDIAMINE INSECTICIDES

Cross Reference to Related Applications

This is a division of my copending application Ser. No. 479,073, filed June 13, 1974, and issued Sept. 23, 1975, as 3,907,892. Application Ser. No. 479,073 was a continuation-in-part of copending application Ser. No. 277,452, filed Aug. 2, 1972, which was in turn a continuation-in-part of my then copending application Ser. No. 47,857, filed June 19, 1970, and of my then copending application Ser. No. 17,865, filed Mar. 9, 1970, and itself a continuation-in-part of my then copending application Ser. No. 803,998, filed Mar. 3, 1969. Each of Applications 803,998, 17,865, 47,857, and 277,452 was abandoned after the filing of the subsequent application in the series.

Summary of the Invention

The present invention is directed to novel ring-substituted N-(2,2-difluoroalkanoyl)-o-phenylenediamine compounds of the formulae:

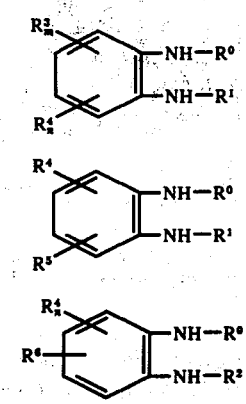

wherein
R° represents a 2,2-difluoroalkanoyl radical of the formula

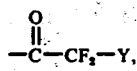

wherein Y represents hydrogen, chlorine, fluorine, difluoromethyl, perfluoroalkyl of $C_1$–$C_6$, or radical of the formula

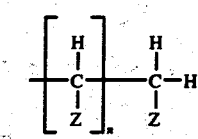

wherein each Z independently represents hydrogen or halogen and n represents 0 or 1;
$R^1$ represents
hydrogen,
radical of the formula

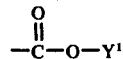

wherein $Y^1$ represents loweralkyl of $C_1$–$C_4$ or phenyl,
benzoyl,
furoyl,
naphthoyl, or
substituted benzoyl of the formula

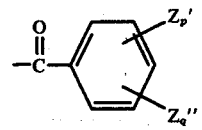

wherein each Z' independently represents halo or nitro, Z" represents loweralkyl or $C_1$–$C_4$ or loweralkoxy of $C_1$–$C_4$, p represents 0, 1, or 2, q represents 0 or 1, and the sum of p and q is 1–3;
$R^2$ represents
R°,
$R^1$,
alkanoyl of $C_1$–$C_8$,
loweralkenoyl of $C_3$–$C_4$,
loweralkynoyl of $C_3$–$C_4$,
halogenated loweralkanoyl of $C_2$–$C_4$ bearing on any position or positions one or more halogen atoms, each independently selected, subject to the limitation that the alpha position bear at least one substituent moiety selected from the group consisting of hydrogen and halogen of atomic weight from 35 to 127, both inclusive;
each $R^3$ independently represents halogen;
$R^4$ represents nitro;
$R^5$ represents trifluoromethyl, difluoromethyl, or difluorochloromethyl, and in compounds of Formula II, $R^4$ and $R^5$ are meta to one another;
$R^6$ represents loweralkylsulfonyl of $C_1$–$C_4$ and is located at the 4 or 5 position, and any $R^4$ group is meta to $R^6$;
m represents 0–4;
n represents 0–1; and in compounds of Formula I, the sum of m and n is an integer of from 1–4;
subject to the further limitation that where $R^1$ or $R^2$ represents hydrogen, the ring position ortho to the —NH-$R^1$ or —NH-$R^2$ group bears one of the designated $R^3$, $R^4$, $R^5$, or $R^6$ moieties. All of the ring-substituted N-(2,2-difluoroalkanoyl)-o-phenylenediamine compounds of the present invention are useful as herbicides. Hence the present invention is directed to methods employing and compositions comprising these novel ring-substituted N-(2,2-difluoroalkanoyl)-o-phenylenediamine compounds as herbicides.

The present ring-substituted N-(2,2-difluoroalkanoyl)-o-phenylenediamine compounds also exhibit insecticidal and arachnicidal activity. Such activity is most pronounced among compounds of Formula II. Hence the present invention is also directed to methods employing these compounds as insecticides.

In addition, the present invention is also directed to combinations of the compounds of the present invention with known herbicides.

Detailed Description of the Invention

For the sake of uniformity, starting materials and products herein are named, where possible, as o-phenylenediamines. In accordance with common nomenclature practice, the identification of various substituent positions is as follows:

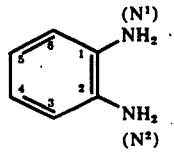

where either nitrogen atom bears an alkanoyl or other ($R^°$, $R^1$, $R^2$) substituent, the ring position numbers are identified as prime numbers to distinguish them from numbers of positions on the $R^°$, $R^1$, or $R^2$ substituent.

In the foregoing definition of the compounds of the present invention, as generally in the present specification and claims, each of the terms "halo" and "halogen," when unqualified but as used both alone and in the composite term "halogenated loweralkanoyl," designates bromine, chlorine, fluorine, or iodine, only.

An essential and distinguishing structural feature of the compounds of the present invention is the 2,2-difluoroalkanoyl-radical ($R^°$); representative such radicals include the following:

difluoroacetyl
trifluoroacetyl
difluorochloroacetyl
pentafluoropropionyl
heptafluorobutyryl
nona-fluorovaleryl
2,2,3,3-tetrafluoropropionyl
undecafluorohexanoyl
tridecafluoroheptanoyl
pentadecafluorooctanoyl
2,2-difluoropropionyl
2,2-difluorobutyryl
2,2-difluoro-3-bromopropionyl
2,2-difluoro-3-chloropropionyl
2,2-difluoro-3,4-dichlorobutyryl
2,2-difluoro-4-bromobutyryl
2,2,3-trifluoropropionyl
2,2,3-trifluorobutyryl
2,2,3,4-tetrafluorobutyryl
2,2-difluoro-3-bromo-4-chlorobutyryl Preferred $R^°$ groups are trifluoroacetyl, difluoroacetyl, difluorochloroacetyl, and 2,2,3,3-tetrafluoropropionyl.

The compounds of the present invention are prepared by introduction of the characteristic 2,2-difluoroalkanoyl group into appropriate corresponding diamine starting materials. Introduction of this group can be achieved by any of numerous available acylation reactions, employing any of several types of acylating agent. The identity of acylating agent is not critical; suitable acylating agents include the 2,2-difluoroalkanoyl halides:

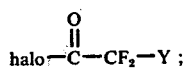

and the 2,2-difluoroalkanoic anhydrides:

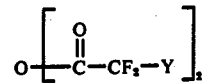

The diamine starting materials with which the acylation reaction is carried out will vary. In the instance of compounds of the present invention wherein $R^1$ is hydrogen or wherein $R^2$ is either hydrogen or the same moiety as is represented by $R^°$, the starting diamine is a compound of one of the following formulae:

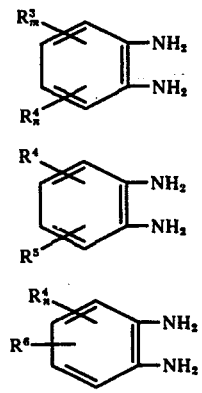

and either one acyl group is introduced (leaving $R^1$ or $R^2$ = hydrogen) or two identical acyl groups are introduced

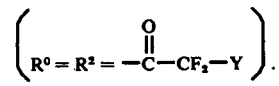

Where, on the other hand, $R^1$ is any other moiety than hydrogen and $R^2$ is any other moiety than hydrogen or the same 2,2-difluoroalkanoyl moiety as is represented by $R^°$, the appropriate diamine starting material is a compound already bearing the desired $R^1$ or $R^2$ moiety:

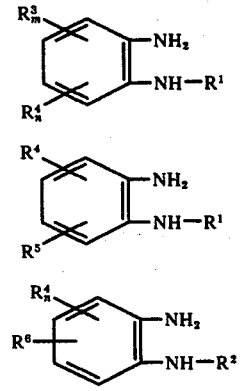

and the characteristic $R^°$ group is similarly introduced by acylation. It is noted that the $R^2$ group can be a 2,2-difluoroalkanoyl group different from that represented by $R^°$, in which instance the groups are introduced sequentially.

While the synthetic routes described foregoing are convenient and preferred, yet other routes can be utilized. Thus, for example, in the instance where $R^1$ represents an acyl group other than a 2,2-difluoroalkanoyl radical, the $R^1$ group is conveniently introduced in some instances after the $R^o$ has already been introduced. However, because of the activating effect on acylation of the alpha fluorine atoms, it is generally preferred that groups other than the 2,2-difluoroalkanoyl moiety already be present when this group is introduced. In the instance where $R^2 =$ formyl, the acylation is conducted with a mixed anhydride of acetic and formic acid. Alternately, other acylating agents by which formyl groups are introduced can be used.

The preparation of amides by the acylating of corresponding amines with various acylating agents is, as noted, a known synthetic method. The present preparations are conducted in accordance with the known procedures for effecting this method. Thus, where the acylating agent is an anhydride, the reaction is conveniently conducted at room temperature; solvent, which can be excess anhydride, except in the case of amides where $R^1$ or $R^2 =$ H, can be utilized. Where an acyl halide is employed as acylating agent, the reaction is necessarily conducted in the presence of a hydrogen halide acceptor and preferably in the presence of an inert solvent, and the reaction mixture is preferably cooled, such as to temperatures of 0°–10° C. In the case of either acylating agent, the product is separated in conventional procedures, and can be purified if desired, likewise in conventional procedures.

The following examples illustrate the synthesis of the compounds of the present invention and will enable those skilled in the art to practice the present invention.

Example 1

$N^1$-TRIFLUOROACETYL-3',4',5',6'-TETRA-CHLORO-o-PHENYLENEDIAMINE 3,4,5,6-Tetrachloro-o-phenylenediamine (2.0 grams) was dissolved in 50 milliliters of benzene and 0.8 milliliter of triethylamine and the solution treated with trifluoroacetic anhydride (1.84 grams). The resulting reaction mixture was then heated to reflux, refluxed for 16 hours, condensed by evaporation to 20 milliliters, and the desired $N^1$-trifluoroacetyl-3',4',5',6'-tetrachloro-o-phenylenediamine product separated by filtration and recrystallized from chloroform, m.p., 245°–47° C.

Example 2

$N^1$-TRIFLUOROACETYL-3'-TRIFLUOROMETHYL-5'-NITRO-o-PHENYLENEDIAMINE

Finely ground 3-trifluoromethyl-5-nitro-o-phenylenediamine (2.2 grams), triethylamine (1.0 ml.), and chloroform (10 milliliters) were mixed and stirred while trifluoroacetic anhydride (2–3 milliliters in chloroform (20 milliliters)) was added. The addition was carried out portionwise over a period of 20 minutes and at room temperature. The resulting reaction mixture was filtered to separate the desired $N^1$-trifluoroacetyl-3'-trifluoromethyl-5'-nitro-o-phenylenediamine product which was recrystallized from benzene, m.p., 201°–02° C.

Analysis, Calc. for $C_9H_5F_6N_3O_3$: C, 34.08; H, 1.58; N, 13.24.

Found: C, 34.24; H, 1.60; N, 13.24.

Example 3

$N^1$-CHLORODIFLUOROACETYL-3'-NITRO-5'-TRIFLUOROMETHYL-o-PHENYLENEDIAMINE

3-Nitro-5-trifluoromethyl-o-phenylenediamine (5.0 grams) was mixed with 15 milliliters of pyridine and the mixture cooled to 0° C. Chlorodifluoroacetyl chloride (3 milliliters) was then added with stirring over a period of 20 minutes. After standing at 20° C. for about 1.5 hours, the reaction mixture was mixed with 150 grams of ice and 20 milliliters of hydrochloric acid, which resulted in the precipitation of the desired $N^1$-chlorodifluoroacetyl-3'-nitro-5'-trifluoromethyl-o-phenylenediamine product. It was separated by filtration and recrystallized from benzene, m.p., 186°–88° C.

Example 4

$N^1$-BENZOYL-$N^2$-TRIFLUOROACETYL-3'-NITRO-5'-TRIFLUOROMETHYL-o-PHENYLENEDIAMINE $N^1$-Benzoyl-3-nitro-5-trifluoromethyl-o-phenylenediamine (3.2 grams) and excess trifluoroacetic anhydride were mixed and allowed to stand overnight. Excess trifluoroacetic anhydride and the corresponding by-product acid were evaporated under vacuum to separate the desired $N^1$-benzoyl-$N^2$-trifluoroacetyl-3'-nitro-5'-trifluoromethyl-o-phenylenediamine product, which, after recrystallization from benzene, melted at 193°–95° C.

Examples 5–27

Other compounds representative of the present invention are readily prepared in the procedures of the foregoing teachings and examples, using analogous starting materials. Such compounds include the following:

$N^1$-Trifluoroacetyl-3'-nitro-5'-trifluoromethyl-o-phenylenediamine, m.p., 194–95° C., prepared by reacting trifluoroacetic anhydride with 3-nitro-5-trifluoromethyl-o-phenylenediamine.

$N^1$-Propionyl-$N^2$-(2,2-difluoro-3-iodopropionyl)-5'-(sec-butylsulfonyl)-o-phenylenediamine, prepared by reacting 2,2-difluoro-3-iodopropionyl chloride with $N^1$-propionyl-5-(sec-butylsulfonyl)-o-phenylenediamine.

$N^1$-Trifluoroacetyl-$N^2$-acetyl-3'-nitro-5'-trifluoromethyl-o-phenylenediamine, m.p., 219–20° C., prepared by reacting trifluoroacetic anhydride with $N^2$-acetyl-3-nitro-5-trifluoromethyl-o-phenylenediamine.

$N^1$, $N^2$-Bis(trifluoroacetyl)-5'-(methylsulfonyl)-o-phenylenediamine, m.p., 179°–81° C, prepared by reacting trifluoroacetic anhydride with 5-(methylsulfonyl)-o-phenylenediamine.

$N^1,N^2$-Bis(2,2-difluorobutyryl)-3'-nitro-5'-trifluoromethyl-o-phenylenediamine, prepared by reacting 2,2-difluorobutyric anhydride with 3-nitro-5-trifluoromethyl-o-phenylenediamine.

$N^1$-Trifluoroacetyl-$N^2$-p-toluoyl-5',6'-dichloro-o-phenylenediamine, prepared by reacting trifluoroacetyl chloride with $N^2$-p-toluoyl-5,6-dichloro-o-phenylenediamine.

$N^1$-Acetyl-$N^2$-trifluoroacetyl-5'-(methylsulfonyl)-o-phenylenediamine, m.p. 200°–01° C., prepared by reacting trifluoroacetic anhydride with $N^1$-acetyl-5-(methylsulfonyl)-o-phenylenediamine.

$N^1$-Difluorochloroacetyl-$N^2$-hexanoyl-5'-(n-propylsulfonyl) o-phenylenediamine, prepared by reacting difluorochloroacetic anhydride with N²-hexanoyl-5-(n-propylsulfonyl)-o-phenylenediamine.

N¹-Trifluoroacetyl-3'-nitro-5'-chloro-o-phenylenediamine, m.p., 184–86°C., prepared by reacting trifluoroacetic anhydride with 3-nitro-5-chloro-o-phenylenediamine.

N¹, N²-Bis(2,2-difluoro-4-bromobutyryl)-3'-nitro-5'-trifluoromethyl-o-phenylenediamine, prepared by reacting 2,2-difluoro-4-bromobutyric anhydride with 3-nitro-5-trifluoromethyl-o-phenylenediamine.

N¹-Acetyl-N²-trifluoroacetyl-3'-nitro-5'-trifluoromethyl-o-phenylenediamine, m.p., 215°–16° C., prepared by reacting trifluoroacetic anhydride with N¹-acetyl-3-nitro-5-trifluoromethyl-o-phenylenediamine.

N¹-(3-Bromopropionyl)-N²-trifluoroacetyl-5'-(ethylsulfonyl)-o-phenylenediamine, prepared by reacting trifluoroacetic anhydride with N¹-(3-bromopropionyl)-5-(ethylsulfonyl)-o-phenylenediamine.

N¹-(2,2-Difluoro-3-bromopropionyl)-N²-(2-chloro-4-tert-butylbenzoyl)-3'-nitro-5'-trifluoromethyl-o-phenylenediamine, prepared by reacting 2,2-difluoro-3-bromopropionyl chloride with N²-(2-chloro-4-tert-butylbenzoyl)-3-nitro-5-trifluoromethyl-o-phenylenediamine.

N¹, N²-Bis(trifluoroacetyl)-3'-nitro-5'-trifluoromethyl-o-phenylenediamine, m.p., 210°–12°C., prepared by reacting trifluoroacetic anhydride with 3-nitro-5-trifluoromethyl-o-phenylenediamine.

N¹-Trifluoroacetyl-N²-(methoxycarbonyl)-5',6'-difluoro-o-phenylenediamine, prepared by reacting trifluoroacetic anhydride with N²-(methoxycarbonyl)-5,6-difluoro-o-phenylenediamine.

N¹-Difluorochloroacetyl-N²-(phenoxycarbonyl)-3'-nitro-5'-difluoromethyl-o-phenylenediamine, prepared by reacting difluorochloroacetic anhydride with N²-(phenoxycarbonyl)-3-nitro-5-difluoromethyl-o-phenylenediamine.

N¹-(3,4-Dichlorobenzoyl)-N²-difluoroacetyl-4'-chloro-o-phenylenediamine, prepared by reacting difluoroacetic anhydride with N¹-(3,4-dichlorobenzoyl)-4-chloro-o-phenylenediamine.

N¹-Pentafluoropropionyl-N²-(5-bromo-m-toluoyl)-3',4',5',6'-tetrachloro-o-phenylenediamine, prepared by reacting pentafluoropropionic anhydride with N²-(5-bromo-m-toluoyl)-3,4,5,6-tetrachloro-o-phenylenediamine.

N¹-Heptafluorobutyryl-N²-(sec-butoxycarbonyl)-4'-bromo-o-phenylenediamine, prepared by reacting heptafluorobutyric anhydride with N²-(sec-butoxycarbonyl)-4-bromo-o-phenylenediamine.

N¹-(2,2-Difluoropropionyl)-N²-(3-nitro-5-isopropoxybenzoyl)-5',6'-dichloro-o-phenylenediamine, prepared by reacting 2,2-difluoropropionyl bromide with N²-(3-nitro-5-isopropoxybenzoyl)-5,6-dichloro-o-phenylenediamine.

N¹-Naphthoyl-N²-trifluoroacetyl-3'-nitro-5'-trifluoromethyl-o-phenylenediamine, m.p., 200°–04° C., prepared by reacting trifluoroacetic anhydride with N¹-naphthoyl-3-nitro-5-trifluoromethyl-o-phenylenediamine.

N¹,N²-Bis(difluoroacetyl)-3'-nitro-5'-difluoromethyl-o-phenylenediamine, prepared by reacting difluoroacetic anhydride with 3-nitro-5-difluoromethyl-o-phenylenediamine.

N¹-Iodoacetyl-N²-trifluoroacetyl-5'-(methylsulfonyl)-o-phenylenediamine, prepared by reacting trifluoroacetic anhydride with N¹-iodoacetyl-5-(methylsulfonyl)-o-phenylenediamine.

Yet other representative compounds of the present invention include the following:

N¹-Trifluoroacetyl-N²-(p-n-butoxybenzoyl)-4'-trifluoromethyl-6'-nitro-o-phenylenediamine, m.p., 172°–74°C.

N¹Trifluoroacetyl-N²-(p-nitrobenzoyl)-4'-trifluoromethyl-6'-nitro-o-phenylenediamine, m.p., 210°–12°C.

N¹-Pentafluoropropionyl-N²-(2,2-dichloropropionyl)-4'-trifluoromethyl-6'-nitro-o-phenylenediamine, m.p. 144–45°C.

N¹-Trifluoroacetyl-N²-(2,2-dichloropropionyl)-4'-trifluoromethyl-6'-nitro-o-phenylenediamine, m.p., 172–73°C.

N¹-Trifluoroacetyl-N²-(2,4-dichloro-6-methoxybenzoyl)-6'-nitro-o-phenylenediamine, m.p., 200–01°C.

N¹-Heptafluorobutyryl-3'-nitro-5'-trifluoromethyl-o-phenylenediamine, m.p., 118°–20°C.

N¹-Trifluoroacetyl-N²-pentafluoropropionyl-4'-trifluoromethyl-6'-nitro-o-phenylenediamine, m.p. 185°–86°C.

N¹-Pentafluoropropionyl-3'-nitro-5'-trifluoromethyl-o-phenylenediamine, m.p., 161°–63°C.

N¹-Trifluoroacetyl-N²-dichlorofluoroacetyl-4'-trifluoromethyl-6'-nitro-o-phenylenediamine, m.p., 163°–64°C.

N¹-Trifluoroacetyl-N²-methoxycarbonyl-4'-trifluoromethyl-6'-nitro-o-phenylenediamine, m.p. 129°–30°C.

N¹-Pentafluoropropionyl-N²-trichloroacetyl-3'-nitro-5'-trifluoromethyl-o-phenylenediamine, m.p. 167°–68°C.

N¹-Difluorochloroacetyl-N²-propionyl-4'-trifluoromethyl-6'-nitro-o-phenylenediamine, m.p., 152°–54°C.

N¹-Pentadecafluorooctanoyl-3'-nitro-5'-trifluoromethyl-o-phenylenediamine, m.p., 111°–13°C.

N¹-Trifluoroacetyl-N²-trichloroacetyl-4'-trifluoromethyl-6'-nitro-o-phenyelendiamine, m.p., 170°–72°C.

N¹-Trifluoroacetyl-N²-benzoyl-3'-trifluoromethyl-5'-nitro-o-phenylenediamine.

N¹-Trifluoroacetyl-N²-naphthoyl-4'-trifluoromethyl-6'-nitro-o-phenylenediamine.

N¹-Trifluoroacetyl-N²-methacryloyl-4'-trifluoromethyl-6'-nitro-o-phenylenediamine.

N¹-Trifluoroacetyl-N²-propioloyl-4'-trifluoromethyl-6'-nitro-o-phenylenediamine.

N¹-Trifluoroacetyl-N²-trichloroacetyl-3'-nitro-5'-(methylsulfonyl)-o-phenylenediamine.

N¹-Pentadecafluorooctanoyl-N²-acetyl-4'-(methylsulfonyl)-o-phenylenediamine.

N¹, N²-Bis(heptafluorobutyryl)-4'-(methylsulfonyl)-o-phenylenediamine.

N¹-Trifluoroacetyl-N²-acryloyl-4'-(methylsulfonyl)-o-phenylenediamine.

N¹-Trifluoroacetyl-N²-propioloyl-4'-(methylsulfonyl)-o-phenylenediamine.

N¹-Trifluoroacetyl-N²-benzoyl-4'-(ethylsulfonyl)-6'-nitro-o-phenylenediamine.

N¹-Pentafluoropropionyl-N²-naphthoyl-4'-(methylsulfonyl)-o-phenylenediamine.

N¹Difluoroacetyl-N²-methoxycarbonyl-4'-(methylsulfonyl)-o-phenylenediamine.

N¹-Heptafluorobutyryl-N²-p-toluoyl-4'-(methylsulfonyl)-6'-nitro-o-phenylenediamine.

$N^1$-Trifluoroacetyl-$N^2$-benzoyl-4',5'-dichloro-o-phenylenediamine.

$N^1$-Trifluoroacetyl-$N^2$-naphthoyl-4'-nitro-o-phenylenediamine.

$N^1$-Trifluoroacetyl-$N^2$-furoyl-5'(methylsulfonyl)-o-phenylenediamine, m.p., 185–87° C.

$N^1$-Difluoroacetyl-$N^2$-furoyl-3'-nitro-5'-trifluoromethyl-o-phenylenediamine.

$N^1$-Chlorodifluoroacetyl-$N^2$-furoyl-4',5'-dichloro-o-phenylenediamine.

$N^2$-(2,2,3,3-Tetrafluoropropionyl)-$N^1$-methoxycarbonyl-3'-nitro-5'-trifluoromethyl-o-phenylenediamine, m.p., 129–30° C.

$N^1$-(2,2,3,3-Tetrafluoropropionyl)-3'-nitro-5'-trifluoromethyl-o-phenylenediamine.

All of the compounds of the present invention are adapted to be employed as herbicides. The compounds can be utilized to achieve broad herbicidal action; hence, in its broadest sense, the present invention is directed to a method which comprises applying to a plant part, which can be a stem, leaf, flower, fruit, root, or seed or other similar reproductive unit of a plant, a growth-inhibiting amount of one of the ring-substituted (2,2-difluoroalkanoyl-o-phenylenediamine compounds of the present invention. However, the compounds can also be utilized to take advantage of selective patterns of herbicidal activity.

As set forth above, the present invention in its broadest sense is directed to a herbicidal method employing one of the present compounds. However, as will be evident to those skilled in the art, a mixture of more than one of the present compounds can also be employed in the practice of the present invention. When employing a mixture, an appropriate reduction should be made in the amount of each individual compound so that the mixture provides only the desired herbicidal effect.

It is not critical to the practice of the present invention that complete destruction of undesirable vegetation be obtained, it being adequate if the growth of the unwanted vegetation is merely inhibited. Especially where selective action is sought, inhibition falling short of actual killing is adequate, particularly when combined with naturally occurring conditions such as limited moisture and the like which more adversely affect the vegetation selectively inhibited than the crop plant.

The compounds of the present invention are suited to a wide variety of herbicidal applications. Thus, for example, at rates which evoke the selective action of the compounds, which rates are defined more completely hereinbelow, the compounds can be used as selective herbicides in crop plants, such as, for example, cotton, corn, sorghum, soybeans, and the like. In such use, application can be made preemergent to both crops and weeds, or, preferably by means of a directed spray application technique, postemergent to the crop plant but both preemergent and postemergent to the weeds. In another application, the compounds can be used to give broad herbicidal action on non-crop land, including intermittently noncrop strips of contour-farmed land. For such usage on so-called fallow land, application can be made in spring to suppress vegetative growth until a fall or following spring planting, or in the fall to suppress vegetative growth until a spring or following fall planting. Furthermore, in another application, the present compounds can be utilized to control weeds in tree crop plantings, such as plantings of the various citrus trees. In all of these various applications, and yet others for which the present compounds are suited, another advantage is that the compounds need not be disced into the soil being treated, it being adequate if one of the compounds, or a formulation containing one of the compounds, is merely spread onto the top surface. However, where desired or convenient, the compounds can be disced into, or otherwise mechanically mixed with the soil. In addition to the foregoing terrestrial embodiments, the present compounds can also be utilized as aquatic herbicides.

The practice of the present invention in any of its numerous embodiments can in some instances be carried out with unmodified compound; however, for good results, it is generally necessary that the compound be employed in modified form, that is, as one component of a composition formulated to implement the plant growth-inhibiting effects. Thus, for example, the active agent can be mixed with water or other liquid or liquids, preferably aided by the usage of a surface active agent. The active agent can also be incorporated on a finely divided solid, which can be a surface active substance, to yield a wettable powder, which can subsequently be dispersed in water or other liquid, or incorporated as part of a dust which can be applied directly. Other methods of formulations are known in the art and can be employed in implementing the present invention.

In carrying out the novel method of the present invention, the exact amount of the active agent employed is not critical and will vary, depending upon the type of growth-inhibiting effect desired, the identity of the plants concerned, the particular active agent used, weather conditions, and the like. In general, a broad growth-inhibiting effect is obtained with rates of from 0.5 to 20 pounds or more of active agent per acre, and such rates are suitable and effective for control of vegetative growth on fallow land. When it is desired to obtain a selective growth-inhibiting effect on weeds in areas containing crop plants such as corn, soybeans, and cotton, rates of from 0.5 to 10 pounds generally give good results. When in the typical mode of operation, the active agent is employed as a composition comprising the agent, the exact concentration of active agent in the composition is not critical, except that the concentration and total amount of formulation employed be adequate to supply the appropriate amount of active agent on a per acre basis. In general, good results are obtained when employing formulations containing the active agent in a concentration of from 0.5 to 10 percent or higher, in the instance of a liquid formulation; and in a concentration of from 1.0 to 5.0 percent or higher, in the instance of a dust, powder, granule, or the like. More concentrated formulations can be prepared and are often preferred in that they can serve, depending upon the particular application contemplated and the particular concentration, both as a concentrated formulation for purposes of shipment, storage, and the like, and as an ultimate treating composition. Thus, for example, formulations often preferably contain a surface active agent and the present active agent, the latter being present in an amount of from 0.5 to 99.5 percent, by weight, or an inert, finely divided solid and the present active agent, the latter being present in an amount of from 1.0 to 99 percent, by weight. Such formulations, as indicated, can be employed directly in certain applications, but can also be diluted and subsequently employed in many other applications.

Liquid compositions containing the desired amount of active agent are prepared by dissolving the substance in an organic liquid or by dispersing the substance in water with or without the aid of a suitable surface active dispersing agent such as an ionic or non-ionic emulsifying agent. Such compositions can also contain modifying substances which serve as a "spreader" and "sticker" on plant foliage. Suitable organic liquid carriers include the agricultural spray oils and the petroleum distillates such as diesel fuel, kerosene, fuel oil naphthas, and Stoddard solvent. Among such liquids, the petroleum distillates are generally preferred. The aqueous compositions can contain one or more water immiscible solvents for the toxicant compound. In such compositions, the carrier comprises an aqueous emulsion, e.g., a mixture of water, emulsifying agent and water immiscible solvent. The choice of dispersing and emulsifying agent and the amount thereof employed is dictated by the nature of the composition and by the ability of the agent to facilitate the dispersion of the active agent in the carrier to produce the desired composition. Dispersing and emulsifying agents which can be employed in the compositions include the condensation products of alkylene oxides with phenols and organic acids, alkyl aryl sulfonates, polyoxyalkylene derivative or sorbitan esters, complex ether alcohols, and the like. Representative surface active agents which are suitably employed in implementing the present invention are identified in U.S. Pats. 3,095,299, second column, lines 25-36; 2,655,447, column 5; and 2,412,510, columns 4 and 5.

In the preparation of dust compositions, the active ingredient is intimately dispersed in and on a finely divided solid such as clay, talc, chalk, gypsum, limestone, vermiculite fines, perlite, and the like. In one method of achieving such dispersion, the finely divided carrier is mechanically mixed or ground with the active agent.

Similarly, dust compositions containing the toxicant compounds can be prepared with various of the solid surface active dispersing agents such as bentonite, fuller's earth, attapulgite and other clays. Depending upon the proportions of ingredients, these dust compositions can be employed as concentrates and subsequently diluted with additional solid surface active dispersing agents or with chalk, talc, or gypsum and the like to obtain the desired amount of active ingredient in a composition adapted to be employed for the suppression of the growth of the plants. Also, such dust compositions can be dispersed in water, with or without the aid of a dispersing agent, to form spray mixtures.

Formulations containing the present active agent are often advantageously further modified by incorporation therein of an effective amount of a surfactant which facilitates the dispersion and spreading of the formulation on the plant leaf surfaces and the incorporation of the formulation by the plant.

In accordance with the present invention, the active agent can be dispersed in soil or other growth media in any convenient fashion. Applications can be carried out by simply mixing with the media, by applying to the surface of soil and thereafter dragging or discing into the soil to the desired depth, or by employing a liquid carrier to accomplish the penetration and impregnation. The application of spray and dust compositions to the surface of soil, or to plant parts or the above ground surfaces of plants can be carried out by conventional methods, e.g., powder dusters, boom and hand sprayers and spray dusters, whether surface or air-borne. However, while such conventional modes of application can be used, they are not required. As above noted, it is an advantage of the present invention that the compounds serving as active agent are active and effective as herbicides when merely placed on the surface of the soil, without any additional step to assist incorporation. Thus, the compounds are of substantially the same efficacy regardless of whether they are applied to the surface only, or whether they are applied to the surface and subsequently disced into the soil.

In a further method, the distribution of the active agent in soil can be accomplished by introducing the agent into the water employed to irrigate the soil. In such procedures, the amount of water is varied with the porosity and water holding capacity of the soil to obtain a desired depth of distribution of the agent.

The compounds of the present invention exhibit low mammalian toxicity relative to corresponding benzimidazoles.

In addition, the present method also comprehends the employment of an aerosol composition containing one or more of the present active agents as an active compound. Such a composition is prepared according to conventional methods wherein the agent is dispersed in a solvent, and the resultant dispersion mixed with a propellant in liquid state. Such variables as the particular agent to be used and the nature of the vegetation which is to be treated will determine the desirability of the solvent and concentration of the agent therein. Examples of suitable solvents are water, acetone, isopropanol, and 2-ethoxyethanol.

Satisfactory results are obtained when the active agent of the present invention, or a composition comprising such active agent, is combined with other agricultural materials intended to be applied to plants, plant parts, or their habitats. Such materials include fertilizers, fungicides, insecticides, other herbicides, soil conditioning agents, and the like.

EXAMPLES 28-31

Various of the compounds to be employed as active agent in accordance with the present invention were evaluated for pre-emergent application to various species of plants. In this evaluation, a soil was prepared consisting of one part masonry sand and one part shredded top soil blended together in a cement mixer. One gallon of this soil was placed in a 25 × 35 cm. galvanized flat and was patted down with a bench brush until level. A three-row marker was used to make 2 ½ cm. deep furrows in approximately two-fifths of the flat. Crop seeds consisting of four kernels of corn, five cotton seeds, and five soybean seeds were placed in these furrows. A four-row template was then placed on the remaining soil and the indicated approximate numbers of each of the following seeds were planted, one species to each section: foxtail (millet), 80-100 seeds; velvetleaf (40-50 seeds); rough pigweed (150-250 seeds); and large crabgrass (100-150 seeds).

Sufficient soil was added to cover the entire flat. Thus, the weed seeds were covered to a depth of about 6 mm. and the crop seeds were covered to a depth of about 3 cm.

In assaying the effect of the composition as preemergent herbicides, a flat prepared as above, taken either on the day of planting or on the next day, was placed in a chamber equipped with a turntable and an air exhaust. The herbicidal composition, either a spray-type emulsion or a wettable powder, was applied to the flat with a modified DeVilbiss atomizer hooked to an air source. Twelve and one-half milliliters of the composition under test were applied to each flat either on the day of planting or the succeeding day. Injury ratings and observations as to type of injury were made eleven to twelve days after treatment. The injury rating scale used was as follows:

0—no injury
1—slight injury
2—moderate injury
3—severe injury
4—death

When more than one determination was carried out at a given rate, an average value was calculated for the injury rating. Each compound evaluated was formulated as a spray by one of the following procedures. In one method the particular compound was wetted by grinding in a mortar with one part of polyoxyethylene sorbitan monolaurate. Five hundred parts of water were added slowly to the resultant creamy paste to give an aqueous dispersion with a surfactant concentration of 0.2 percent. This dispersion was entirely satisfactory for spray application. In a second procedure the compound was dissolved in one volume of acetone, and the acetone solution was diluted with nineteen volumes of water containing 0.1 percent of polyoxyethylene sorbitan monolaurate.

In the following table setting forth the results of the evaluation, column 1 gives the name of the component under test; column 2, the rate in pounds per acre at which the compound was applied to the test flat; and the remaining columns, the injury to the particular plant seeds or seedlings as measured by the foregoing scale.

TABLE I

| Injury Rating on Preemergent Treatment | | | | | | | | |
|---|---|---|---|---|---|---|---|---|
| Compound | Lbs./ Acre | Corn | Cotton | Soybean | Crabgrass | Pigweed | Foxtail | Velvet Leaf |
| $N^1$-Trifluoroacetyl-3′,4′,5′,6′-tetrachloro-o-phenylenediamine | 8 | 1 | 0 | 0 | 4 | 4 | 2 | 1 |
| $N^1$-Trifluoroacetyl-3′-nitro-5′-chloro-o-phenylenediamine | 8 | 1 | 0 | 1 | 4 | 4 | 2 | 3 |
| $N^1,N^3$Bis(trifluoroacetyl)-5′-(methylsulfonyl)-o-phenylenediamine | 8 | 1 | 1 | 2 | 3 | 4 | 3 | 3 |
| $N^1$-trifluoroacetyl-3′-nitro-5′-trifluoromethyl-o-phenylenediamine | 8 | 0 | 0 | 2 | 4 | 4 | 3 | 3 |

EXAMPLES 32–35

Representative compounds of the present invention were evaluated for postemergent application to plants including corn and several weed species. The evaluation was carried out in accordance with the procedures of Examples 28–31 except that the test solutions were applied about 9–12 days after the preparation and seeding of the flats. The results are as set forth in the following table:

TABLE II

| Injury Rating on Postemergent Treatment | | | | | | |
|---|---|---|---|---|---|---|
| Compound | Lbs./ Acre | Corn | Crabgrass | Pigweed | Foxtail | Velvet Leaf |
| $N^1$-Acetyl-$N^2$-trifluoroacetyl-3′-nitro-5′-trifluoromethyl-o-phenylenediamine | 8 | 0 | 2 | 4 | 3 | 4 |
|  | 4 | 1 | 2 | 4 | 4 | 4 |
|  | 2 | 0 | 3 | 4 | 2 | 4 |
| $N^1$-Trifluoroacetyl-3′-nitro-5′-trifluoromethyl-o-phenylenediamine | 8 | 1 | 4 | 4 | 4 | 4 |
| $N^1$-Trifluoroacetyl-3′-nitro-5′-chloro-o-phenylenediamine | 8 | 1 | 3 | 4 | 4 | 4 |
|  | 4 | 2 | 4 | 4 | 4 | 4 |
|  | 2 | 1 | 4 | 4 | 4 | 4 |
|  | 1 | 1 | 4 | 4 | 3 | 4 |
| $N^1,N^2$-Bis(trifluoroacetyl)-5′-(methylsulfonyl)-o-phenylenediamine | 8 | 2 | 4 | 4 | 3 | 4 |
|  | 4 | 1 | 4 | 4 | 4 | 3 |
|  | 2 | 1 | 4 | 4 | 4 | 2 |

EXAMPLE 36

$N^2$-(2,2,3,3-Tetrafluoropropionyl)-$N^1$-methoxycarbonyl- 3′-nitro-5′-trifluoromethyl-o-phenylenediamine was evaluated as a postemergent herbicide. The evaluation was carried out in accordance with the procedures reported in Examples 28–35, but with a single, higher application rate (15 pounds per acre) and with different species (tomato, crabgrass, pigweed).

The specified compound gave a complete kill of each of the named species.

EXAMPLES 37–84

Essentially the same results as those reported in foregoing Examples 28–35 are obtained when evaluating the following other representative compounds of the present invention:

$N^1$-Propionyl-$N^2$-(2,2-difluoro-3-iodopropionyl)-5′-(sec-butylsulfonyl)-o-phenylenediamine $N^1,N^2$-Bis(2,2-difluorobutyryl)-3′-nitro-5′-trifluoromethyl- o-phenylenediamine $N^1$-Trifluoroacetyl-$N^2$-p-toluoyl-5',6'-dichloro-o-phenylenediamine $N^1$-Difluorochloroacetyl-$N^2$-hexanoyl-5'-(n-propylsulfonyl)- o-phenylenediamine $N^1,N^2$-Bis(2,2-difluoro-4-bromobutyryl)3'-nitro-5'-trifluoromethyl-o-phenylenediamine $N^1$-Acetyl-$N^2$-trifluoroacetyl-3'-nitro-5'-trifluoromethyl- o-phenylenediamine $N^1$-(3-Bromopropionyl)-$N^2$-trifluoroacetyl-5'-(ethylsulfonyl)- o-phenylenediamine $N^1$-(2,2-Difluoro-3-bromopropionyl)-$N^2$-(2-chloro-4-tert-butylbenzoyl)-3'-nitro-5'-trifluoromethyl-o-phenylenediamine $N^1$-Trifluoroacetyl-$N^2$-(methoxycarbonyl)-5',6'-difluoro- o-phenylenediamine $N^1$-Difluorochloroacetyl-$N^2$-(phenoxycarbonyl)-3'-nitro- 5'-(difluoromethyl)-o-phenylenediamine $N^1$-(3,4-Dichlorobenzoyl)-$N^2$-difluoroacetyl-4'-chloro- o-phenylenediamine $N^1$-Pentafluoropropionyl-$N^2$-(5-bromo-m-toluoyl)-3',4',5', 6'-tetrachloro-o-phenylenediamine $N^1$-Heptafluorobutyryl-$N^2$-(sec-butoxycarbonyl)-4'-bromo- o-phenylenediamine $N^1,N^2$-Bis(difluoroacetyl)3'-nitro-5'-difluoromethyl-o- phenylenediamine $N^1$-Iodacetyl-$N^2$-trifluoroacetyl-5'-(methylsulfonyl)-o- phenylenediamine $N^1$-Naphthoyl-$N^2$-trifluoroacetyl-3'-nitro-5'-trifluoromethyl- o-phenylenediamine $N^1$-Trifluoroacetyl-$N^2$-(p-n-butoxybenzoyl)-4'-trifluoromethyl- 6'-nitro-o-phenylenediamine $N^1$-Trifluoroacetyl-$N^2$-(p-nitrobenzoyl)-4'-trifluoromethyl- 6'-nitro-o-phenylenediamine $N^1$-Pentafluoropropionyl-$N^2$-(2,2-dichloropropionyl)-4'-trifluoromethyl-6'-nitro-o-phenylenediamine $N^1$-Trifluoroacetyl-$N^2$-(2,2-dichloropropionyl)-4'-trifluoromethyl- 6'-nitro-o-phenylenediamine $N^1$-Trifluoroacetyl-$N^2$-(2,4-dichloro-6-methoxybenzoyl)- 6'-nitro-o-phenylenediamine $N^1$-Heptafluorobutyryl-3'-nitro-5'-trifluoromethyl-o-phenylenediamine $N^1$-Trifluoroacetyl-$N^2$-pentafluoropropionyl-4'-trifluoromethyl- 6'-nitro-o-phenylenediamine $N^1$-Pentafluoropropionyl-3'-nitro-5'-trifluoromethyl-o- phenylenediamine $N^1$-Trifluoroacetyl-$N^2$-dichlorofluoroacetyl-4'-trifluoromethyl- 6'-nitro-o-phenylenediamine $N^1$-Trifluoroacetyl-$N^2$-methoxycarbonyl-4'-trifluoromethyl- 6'-nitro-o-phenylenediamine $N^1$-Pentafluoropropionyl-$N^2$-trichloroacetyl-3'-nitro-5'-trifluoromethyl-o-phenylenediamine $N^1$-Difluorochloroacetyl-$N^2$-propionyl-4'-trifluoromethyl- 6'-nitro-o-phenylenediamine $N^1$-Pentadecafluorooctanoyl-3'-nitro-5'-trifluoromethyl- o-phenylenediamine $N^1$-Trifluoroacetyl-$N^2$-trichloroacetyl-4'-trifluoromethyl- 6'-nitro-o-phenylenediamine $N^1$-Trifluoroacetyl-$N^2$-benzoyl-3'-trifluoromethyl-5'-nitro-o-phenylenediamine $N^1$-Trifluoroacetyl-$N^2$-naphthoyl-4'-trifluoromethyl-6'-nitro-o-phenylenediamine $N^1$-Trifluoroacetyl-$N^2$-methacryloyl-4'-trifluoromethyl-6-nitro-o-phenylenediamine $N^1$-Trifluoroacetyl-$N^2$-propioloyl-4'-trifluoromethyl-6'-nitro-o-phenylenediamine $N^1$-Trifluoroacetyl-$N^2$-trichloroacetyl-3'-nitro-5'-(methylsulfonyl)-o-phenylenediamine $N^1$-Pentadecafluorooctanoyl-$N^2$-acetyl-4'-(methylsulfonyl)- o-phenylenediamine $N^1,N^2$-Bis(heptafluorobutyryl)-4'-(methylsulfonyl)-o- phenylenediamine $N^1$-Trifluoroacetyl-$N^2$-acryloyl-4'-(methylsulfonyl)-o- phenylenediamine $N^1$-Trifluoroacetyl-$N^2$-propioloyl-4'-(methylsulfonyl)-o- phenylenediamine $N^1$-Trifluoroacetyl-$N^2$-benzoyl-4'-(ethylsulfonyl)-6'-nitro-o-phenylenediamine $N^1$-Pentafluoropropionyl-$N^2$-naphthoyl-4'-(methylsulfonyl)- o-phenylenediamine $N^1$-Difluoroacetyl-$N^2$-methoxycarbonyl-4'-(methylsulfonyl)- o-phenylenediamine $N^1$-Heptafluorobutyryl-$N^2$-p-toluoyl-4'-(methylsulfonyl)- 6'-nitro-o-phenylenediamine $N^1$-Trifluoroacetyl-$N^2$-benzoyl-4',5'-dichloro-o-phenylenediamine $N^1$-Trifluoroacetyl-$N^2$-naphthoyl-4'-nitro-o-phenylenediamine $N^1$-Trifluoroacetyl-$N^2$-furoyl-5'-(methylsulfonyl)-o-phenylenediamine $N^1$-Difluoroacetyl-$N^2$-furoyl-3'-nitro-5'-trifluoroacetyl- o-phenylenediamine $N^1$-Chlorodifluoroacetyl-$N^2$-furoyl-4',5'-dichloro-o-phenylenediamine The compounds of the present invention also exhibit insecticidal and arachnicidal activity. This activity is most pronounced among compounds of Formula II. The compounds of these formulae are useful for the control of insect and arachnid pests, and, with proper selection of rates to avoid phytotoxicity, can be used for the control of those insect and arachnid pests found on the roots or aerial portion of plants. These compounds are active, for example, against such arachnids as red spider mite, citrus mite, two-spotted spider mite, Pacific mite, clover mite, fowl mite, various species of ticks, and various species of spiders. The compounds of this sub-genus are also active against insects of the various orders including Mexican bean beetle, boll weevil, corn rootworm, cereal leaf beetle, flea beetles, borers, Colorado potato beetle, grain beetles, alfalfa weevil, carpet beetle, confused flour beetle, powder post beetle, wireworms, rice weevil, rose beetle, plum curculio, white grubs, melon aphid, rose aphid, white fly, grain aphid, corn leaf aphid, pea aphid, mealybugs, scales, leafhoppers, citrus aphid, spotted alfalfa aphid, green peach aphid, bean aphid, milkweed bug, tarnished plant bug, box elder bug, bed bug, squash bug, chinch bug, house fly, yellow fever mosquito, stable fly, horn fly, cabbage maggot, carrot rust fly, Southern armyworm, codling moth, cutworm, clothes moth, Indianmeal moth, leafrollers, corn earworm, European corn borer, cabbage looper, cotton bollworm, bagworm, sod webworm, fall armyworm, German cockroach, and American cockroach.

In addition to utilization for the control of pests on plants, the compounds of this sub-genus of the present invention can also be included in inks, adhesives, soaps, polymeric materials, cutting oils or in oil or latex paints. Also, the products can be distributed in textiles, cellulose materials, or in grains, or can be employed in the impregnation of wood and lumber. Additionally, they can be applied to seeds. In yet other procedures, the products can be vaporized or sprayed or distributed as aerosols into the air, or onto surfaces in contact with the air. In such applications, the compounds manifest the useful properties hereinbefore described.

The methods of the present invention comprise contacting an insect or arachnid with an inactivating amount of one of the compounds of the present sub-genus. Contacting can be effected by application of one or more of the products to a habitat of the insect or arachnid. Representative habitats include soil, air, water, food, vegetation, inert objects, stored matter such as grains, other animal organisms, and the like. The inactivation can be lethal, immediately, or with delay, or can be a sub-lethal one in which the inactivated insect or arachnid is rendered incapable of carrying out one or more of its normal life processes. Among known insecticides, this latter situation typically prevails when one of the systems of the organism, often the nervous system, is seriously disturbed; however, the precise mechanism by which the compounds constituting the present active agent work is not yet known, and the insecticidal and arachnicidal method of the present invention is not limited by any mode of operations.

The utilization of an inactivating amount of one of the compounds of the sub-genus is critical to the insecticidal and arachnicidal method of the present invention. The inactivating amount can sometimes be administered by employing the compound in unmodified form. Frequently, however, the desirable insecticidal and arachnicidal properties of the compounds of the sub-genus can be utilized only, as in the instance of the herbicidal properties, when one or more of the compounds is formulated with one or more adjuvant substances. Reference is made to the discussion hereinabove concerning compositions and adjuvants. Where the insecticidal and arachnicidal method is practiced for the control of plant-attacking insects and arachnids, it is preferred that any adjuvants be essentially non-phytotoxic in the composition to be used in implementing the method.

The exact concentration of one or more of the compounds of the sub-genus of the present invention in a composition thereof with one or a plurality of adjuvants can vary; it is necessary only that one or more of the products be present in such amount as to make possible the application of an inactivating dosage to an insect or arachnid. In many situations, a composition comprising 0.000001 percent of the present active agent is effective for the administration of an inactivating amount thereof to insect and arachnid pest organisms. Compositions having a higher concentration of active agent, such as a concentration of from 0.000001 to 0.5 percent, can of course be employed. In still other operations, compositions containing from 0.5 to 98 percent by weight of one compound or from 0.5 to 98 percent of a total of more than one compound, are conveniently employed. Such compositions are adapted to be employed as treating compositions and applied to insects and arachnids and to their habitats, or to be employed as concentrates and subsequently diluted with additional adjuvant to produce ultimate treating compositions.

When operating in accordance with the present invention, one or more of the compounds of the sub-genus or a composition containing one or more of the compounds is applied to the pests to be controlled directly, or by means of application to a portion or portions of their habitat in any convenient manner, for example, by means of hand dusters or sprayers or by simple mixing with the food to be ingested by the organisms. Application to the foliage of plants is conveniently carried out with power dusters, boom sprayers, and fog sprayers. In such foliar applications, the employed compositions should not contain any appreciable amounts of any phytotoxic diluents. In large-scale operations, dusts, or low-volume sprays, can be applied from an airplane. The present invention also comprehends the employment of compositions comprising one or more of the compounds of the sub-genus, an adjuvant, and one or more biologically active materials, such as other insecticides, fungicides, miticides, bactericides, nematocides, and the like.

EXAMPLE 85

Compounds evaluated for the control of insects and arachnids, as reported in the following examples, were formulated in accordance with the following procedure. Initially, 55 grams of a mixture of two nonionic sulfonate emulsifiers were mixed with 1 liter of cyclohexanone. Of the resulting mixture, 0.9 milliliter was subsequently further mixed with 90 milligrams of the subject compound and diluted with distilled water to 90 milliliters, containing the subject compound at a concentration of 1000 parts per million. For evaluation at lower concentrations, the mixture was further diluted with a dilution composition consisting of 4 liters of distilled water and a total of 1.8 milliliter of the same two nonionic sulfonate emulsifiers.

The insecticidal and arachnicidal activity of the compounds of this invention is illustrated by the following tests against representative insects and arachnids.

Test Methods

Mexican Bean Beetle -

*Epilachna varivestis* (Coleoptera)

Cuttings of four six-day-old Bountiful snap bean plants containing two leaves with approximately 5 square inches of leaf surface were placed in water. The leaves were sprayed to wetting with about 5–10 ml. of a formulation containing a predetermined level of the test compound. Half of the formulation was sprayed on the top surface and half on the bottom surface of the leaf using a DeVilbiss atomizer at 10 psi held at a distance of about 18 inches from the leaf. After the leaves had dried, they were cut from the stem and placed separately in petri dishes. Ten third instar, non-molting Mexican bean beetle larvae grown on Bountiful snap beans were placed on each leaf. Controls consisted of two leaves sprayed with 5 ml. of a 500 ppm. formulation of S-(1,2-dicarbethoxyethyl) O,O-dimethyl phosphorodithicate (reference standard), two leaves sprayed with the formulation without the active ingredient and two leaves were held as untreated controls. After 48 hours, a mortality count was made and the amount of feeding noted. Moribund larvae were counted as dead. The following toxicity rating scale was used:

| Percent Dead | Rating |
|---|---|
| 0–10 | 0 |
| 11–20 | 1 |
| 21–30 | 2 |
| 31–40 | 3 |
| 41–50 | 4 |
| 51–60 | 5 |
| 61–70 | 6 |
| 71–80 | 7 |
| 81–90 | 8 |
| 91–100 | 9 |

Southern Armyworm -

*Prodenia eridania* (Lepidoptera)

Ten uniform Southern armyworm larvae about 1-1.5 cm. in length, grown on Henderson lima beans, were placed on excized bean leaves in petri dishes. The bean leaves were obtained and sprayed with the insecticide in the same way as were the snap bean leaves in the Mexican bean beetle test. The reference standards in this instance were leaves sprayed with 5 ml. of 100 ppm. DDT solution. Mortality counts were made 48 hours after spraying and again moribund larvae were counted as dead. Missing larvae which had probably been eaten were considered alive. The same rating scale was used as in the Mexican bean beetle test.

Melon Aphid -

*Aphis gossypii* (Hemiptera)

Four blue hubbard squash seeds were planted per container in vermiculite and the containers watered from the bottom. After six days, the two weakest plants were cut off and one cotyledon and the primary leaves removed from each of the two remaining plants. The remaining cotyledon was infested with 100 melon aphids from a stock colony by pinning the cotyledon against an aphid-infested squash cotyledon from the colony and allowing the aphids to transfer. After transfer, the colony leaf was removed. Forty-eight hours later, the infested leaves were sprayed to wetting with formulations containing graded amounts of the insecticide using a DeVilbiss atomizer at 10 psi held at 12-15 inches from the plant. Controls consist of two infested, unsprayed squash plants and two infested plants sprayed to wetting with a formulation containing 100 ppm. of S-(1,2-dicarbethoxyethyl) O,O-dimethyl phosphorodithioate as a reference standard. The mortality was estimated 24 hours after spraying by observation using a 10-power dissecting microscope. The same rating scale was used as before.

Two-Spotted Spider Mite -

*Tetranychus urticae* (Acarina)

Two-spotted spider mites were raised on green bean plants, then transferred to squash plants. The squash plants were maintained for two days so that the infestation was well established. The infected squash plants were then sprayed with a test formulation containing the subject compound as in the preceding test methods. Mortality was determined by estimation 48 hours after spraying. The same rating scale was used as in other test procedures.

Milkweed Bug -

*Oncopelitis fasciatus* (Hemiptera)

Ten adult milkweed bugs were chilled and placed in a test cage. The cages containing the bugs were sprayed with 5 ml. of a test formulation containing a predetermined amount of the insecticide, using a DeVilbiss atomizer at 10 psi held 33 inches from the top of the cage. After the cage had been allowed to dry, the bugs were fed and watered for 48 hours. A formulation containing 500 ppm. of S-(1,2-dicarbethoxyethyl) O,O-dimethyl phosphorodithioate was used as a reference standard and two unsprayed cages were kept as controls. Mortality counts were made 48 hours after spraying. Moribund adults were considered dead. The same rating scale was employed as before.

House Fly -

*Musca domestica* (Diptera)

Rearing cages containing four-day-old adult house flies were chilled at 35°-40° F. for about 1 hour. One hundred flies were transferred from the rearing cage to each test cage using a small scoop. The caged flies were kept for 1-2 hours at 70°-80° F. The cages were sprayed in the same manner as described for the milkweed bug with 5 ml. of the test formulation. Two unsprayed cages were held as controls and two cages were sprayed with a 50 ppm. DDT formulation as a reference standard. Mortality counts were made 24 hours after spraying. All flies that did not fly or did not walk up from the bottom of the cage were considered moribund. The same rating scale was employed as heretofore.

Boll Weevil -

*Anthonomus grandis* (Coleoptera)

The procedure was identical to that employed for the Mexican bean beetle and the Southern armyworm, except that 10 adult boll weevils were placed on cotton leaves that had been dipped into formulations of the test compounds. The same rating scale was used.

Test Results

EXAMPLES 86-93

EVALUATION OF COMPOUNDS AGAINST MEXICAN BEAN BEETLE

Various compounds of the sub-genus of the present invention were evaluated in accordance with the test method described above against Mexican Bean Beetle. The compounds so evaluated, the rates employed, and the results of the evaluation are as set forth in the following table. Where more than one evaluation was carried out at a given rate, the result reported for that rate is an average of the several results.

TABLE IV

| Compound | Rate in Parts Per Million | Toxicity Rating Against Mexican Bean Beetle |
|---|---|---|
| $N^1$, $N^2$-Bis(trifluoroacetyl)-3'-nitro-5'-trifluoromethyl-o-phenylenediamine. | 1000 | 9.0 |
|  | 500 | 9.0 |
|  | 250 | 9.0 |
|  | 100 | 9.0 |
|  | 50 | 6.5 |
| $N^1$-Trifluoroacetyl-3'-nitro-5'-trifluoromethyl-o-phenylenediamine | 1000 | 9.0 |
|  | 500 | 9.0 |
|  | 250 | 9.0 |
|  | 100 | 9.0 |
|  | 50 | 9.0 |
| $N^1$-Acetyl-$N^2$-trifluoroacetyl-3'-nitro-5'-trifluoromethyl-o-phenylenediamine | 1000 | 9.0 |
|  | 500 | 9.0 |
|  | 250 | 7.5 |
|  | 100 | 9.0 |
|  | 50 | 8.0 |
| $N^1$-Trifluoroacetyl-$N^2$-(2,2-dichloropropionyl)-4'-trifluoromethyl-6'-nitro-o-phenylenediamine | 1000 | 8.5 |
|  | 500 | 9.0 |
|  | 250 | 9.0 |
|  | 100 | 9.0 |
|  | 50 | 8.5 |
| $N^1$-Trifluoroacetyl-$N^2$-pentafluoropropionyl-4'-trifluoromethyl-6'-nitro-o-phenylenediamine | 1000 | 9.0 |
|  | 500 | 9.0 |
|  | 250 | 9.0 |
|  | 100 | 9.0 |
|  | 50 | 8.5 |
| $N^1$-Trichloroacetyl-$N^2$-trifluoroacetyl-3'-nitro-5'-trifluoromethyl- | 1000 | 9.0 |

TABLE IV-continued

| Compound | Rate in Parts Per Million | Toxicity Rating Against Mexican Bean Beetle |
|---|---|---|
| o-phenylenediamine $N^1$-Difluorochloroacetyl-3'-nitro-5'-trifluoromethyl-o-phenylenediamine | 1000 | 9.0 |
| | 500 | 9.0 |
| | 250 | 9.0 |
| | 100 | 8.0 |
| | 50 | 9.0 |
| $N^1$-Benzoyl-$N^2$-trifluoroacetyl-3'-nitro-5'-trifluoromethyl-o-phenylenediamine | 1000 | 7.0 |
| | 500 | 9.0 |
| | 250 | 7.5 |

EXAMPLES 94–95

EVALUATION OF COMPOUNDS AGAINST SOUTHERN ARMYWORM

Various compounds of the sub-genus of the present invention were evaluated in accordance with the test method described above against Southern armyworm. The compounds so evaluated, the rates employed, and the results of the evaluation are as set forth in the following table. Where more than one evaluation was carried out at a given rate, the result reported for that rate is an average of the several results.

TABLE V

| Compound | Rate in Parts Per Million | Toxicity Rating Against Southern Armyworm |
|---|---|---|
| $N^1$-Trichloroacetyl-$N^2$-trifluoroacetyl-3'-nitro-5'-trifluoromethyl-o-phenylenediamine | 1000 | 9.0 |
| $N^1$-Difluorochloroacetyl-3'-nitro-5'-trifluoromethyl-o-phenylenediamine | 1000 | 8.5 |

EXAMPLES 96–99

EVALUATION OF COMPOUNDS AGAINST MELON APHID

Various compounds of the sub-genus of the present invention were evaluated in accordance with the test method described above against Melon Aphid. The compounds so evaluated, the rates employed, and the results of the evaluation are as set forth in the following table. Where more than one evaluation was carried out at a given rate, the result reported for that rate is an average of the several results.

TABLE VI

| Compound | Rate in Parts per Million | Toxicity Rating Against Melon Aphid |
|---|---|---|
| $N^1,N^2$-Bis(trifluoroacetyl)-3'-nitro-5'-trifluoromethyl-o-phenylenediamine | 1000 | 9.0 |
| | 500 | 8.0 |
| | 250 | 7.5 |
| | 100 | 7.0 |
| $N^1$-Trifluoroacetyl-3'-nitro-5'-trifluoromethyl-o-phenylenediamine | 1000 | 9.0 |
| | 500 | 9.0 |
| | 250 | 9.0 |
| | 100 | 8.0 |
| | 50 | 7.0 |
| $N^1$-Difluorochloroacetyl-3'-nitro-5'-trifluoromethyl-o-phenylenediamine | 1000 | 9.0 |
| | 500 | 9.0 |
| | 250 | 8.5 |
| | 100 | 8.0 |
| $N^1$-Trifluoroacetyl-3'-trifluoromethyl-5'-nitro-o-phenylenediamine | 1000 | 9.0 |
| | 500 | 9.0 |
| | 250 | 9.0 |

EXAMPLES 100–105

EVALUATION OF COMPOUNDS AGAINST TWO-SPOTTED SPIDER MITE

Various compounds of the sub-genus of the present invention were evaluated in accordance with the test method described above against Two-spotted Spider Mite. The compounds so evaluated, the rates employed, and the results of the evaluation are as set forth in the following table.

TABLE VII

| Compound | Rate in Parts Per Million | Toxicity Rating Against Two-Spotted Spider Mite |
|---|---|---|
| $N^1,N^2$-Bis(trifluoroacetyl)-3'-nitro-5'-trifluoromethyl-o-phenylenediamine | 1000 | 9.0 |
| | 500 | 9.0 |
| | 250 | 9.0 |
| | 100 | 9.0 |
| | 50 | 9.0 |
| $N^1$-Trifluoroacetyl-3'-nitro-5'-trifluoromethyl-o-phenylenediamine | 1000 | 9.0 |
| | 500 | 9.0 |
| | 250 | 9.0 |
| | 100 | 9.0 |
| | 50 | 8.5 |
| $N^1$-Trichloroacetyl-$N^2$-trifluoroacetyl-3'-nitro-5'-trifluoromethyl-o-phenylenediamine | 1000 | 9.0 |
| $N^1$-Pentafluoropropionyl-3'-nitro-5'-trifluoromethyl-o-phenylenediamine | 1000 | 9.0 |
| | 500 | 9.0 |
| | 250 | 9.0 |
| | 100 | 9.0 |
| | 50 | 8.5 |
| $N^1$-Difluorochloroacetyl-3'-nitro-5'-trifluoromethyl-o-phenylenediamine | 1000 | 9.0 |
| | 500 | 9.0 |
| | 250 | 9.0 |
| | 100 | 8.0 |

TABLE VII-continued

| Compound | Rate in Parts Per Million | Toxicity Rating Against Two-Spotted Spider Mite |
|---|---|---|
|  | 50 | 9.0 |
| N$^1$-Trifluoroacetyl-3'-trifluoromethyl-5'-nitro-o-phenylenediamine | 1000 | 9.0 |
|  | 500 | 9.0 |
|  | 250 | 9.0 |
|  | 100 | 9.0 |
|  | 50 | 8.0 |

EXAMPLES 106–109

EVALUATION OF COMPOUNDS AGAINST MILKWEED BUG

Various compounds of the sub-genus of the present invention were evaluated in accordance with the test method described above against Milkweed Bug. The compounds so evaluated, the rates employed and the results of the evaluation are as set forth in the following table:

TABLE VIII

| Compound | Rate in Parts Per Million | Toxicity Rating Against Milkweed Bug |
|---|---|---|
| N$^1$-Trifluoroacetyl-3'-nitro-5'-trifluoromethyl-o-phenylenediamine | 1000 | 9.0 |
|  | 500 | 9.0 |
|  | 250 | 9.0 |
|  | 100 | 9.0 |
|  | 50 | 8.0 |
| N$^1$-Difluorochloroacetyl-3'-nitro-5'-trifluoromethyl-o-phenylenediamine | 1000 | 9.0 |
|  | 500 | 9.0 |
|  | 250 | 9.0 |
|  | 100 | 9.0 |
| N$^1$-Trifluoroacetyl-3'-trifluoromethyl-5'-nitro-o-phenylenediamine | 1000 | 9.0 |
|  | 500 | 9.0 |
|  | 250 | 9.0 |
| N$^1$-Heptafluorobutyryl-3'-nitro-5'-trifluoromethyl-o-phenylenediamine | 1000 | 9.0 |
|  | 500 | 9.0 |
|  | 250 | 9.0 |
|  | 100 | 9.0 |
|  | 50 | 9.0 |

EXAMPLES 110–114

EVALUATION OF COMPOUNDS AGAINST HOUSE FLY

Various compounds of the sub-genus of the present invention were evaluated in accordance with the test method described above against House Fly. The compounds so evaluated, the rates employed, and the results of the evaluations are as set forth in the following table. Where more than one evaluation was carried out, the result reported for that rate is an average of the several results.

TABLE IX

| Compound | Rate in Parts Per Million | Toxicity Rating Against House Fly |
|---|---|---|
| N$^1$,N$^2$-Bis(trifluoroacetyl)-3'-nitro-5'-(trifluoromethyl)-o-phenylenediamine | 1000 | 9.0 |
|  | 500 | 9.0 |
|  | 250 | 9.0 |
|  | 100 | 9.0 |
|  | 50 | 9.0 |
| N$^1$-Trifluoroacetyl-3'-nitro-5'-trifluoromethyl-o-phenylenediamine | 1000 | 9.0 |
|  | 500 | 9.0 |
|  | 250 | 9.0 |
|  | 100 | 9.0 |
|  | 50 | 8.5 |
| N$^1$-Acetyl-N$^2$-trifluoroacetyl-3'-nitro-5'-trifluoromethyl-o-phenylenediamine | 1000 | 8.5 |
|  | 500 | 9.0 |
|  | 250 | 9.0 |
|  | 100 | 9.0 |
|  | 50 | 9.0 |
| N$^1$-Trifluoroacetyl-N$^2$-acetyl-3'-nitro-5'-trifluoromethyl-o-phenylenediamine | 1000 | 9.0 |
|  | 500 | 9.0 |
|  | 250 | 9.0 |
|  | 100 | 8.0 |
| N$^1$-Difluorochloroacetyl-3'-nitro-5'-trifluoromethyl-o- | 500 | 9.0 |

TABLE IX-continued

| Compound | Rate in Parts Per Million | Toxicity Rating Against House Fly |
|---|---|---|
| phenylenediamine | 250 | 9.0 |
|  | 100 | 9.0 |
|  | 50 | 9.0 |

EXAMPLES 115–119

EVALUATION OF COMPOUNDS AGAINST BOLL WEEVIL

Various compounds of the sub-genus of the present invention were evaluated in accordance with the test method described above against Boll Weevil. The compounds so evaluated, the rates employed, and the results obtained are as set forth in the following table. Where more than one evaluation was carried out, the result reported for that rate is an average of the several results.

TABLE X

| Compound | Rate in Parts Per Million | Toxicity Rating Against Boll Weevil |
|---|---|---|
| $N^1$-Trifluoroacetyl-$N^2$-(2,2-dichloropropionyl)-4'-trifluoromethyl-6'-nitro-o-phenylenediamine | 1000 | 9.0 |
|  | 500 | 8.5 |
|  | 250 | 9.0 |
|  | 100 | 8.0 |
|  | 50 | 8.0 |
|  | 25 | 8.5 |
| $N^1$-Heptafluorobutyryl-3'-nitro-5'-trifluoromethyl-o-phenylenediamine | 1000 | 9.0 |
|  | 500 | 9.0 |
|  | 250 | 9.0 |
|  | 100 | 9.0 |
|  | 50 | 9.0 |
|  | 25 | 9.0 |
| $N^1$-Trifluoroacetyl-$N^2$-pentafluoropropionyl-4'-trifluoromethyl-6'-nitro-o-phenylenediamine | 1000 | 9.0 |
|  | 500 | 9.0 |
|  | 250 | 9.0 |
|  | 100 | 9.0 |
|  | 50 | 9.0 |
|  | 25 | 9.0 |
|  | 10 | 9.0 |
| $N^1$-Pentafluoropropionyl-3'-nitro-5'-trifluoromethyl-o-phenylenediamine | 1000 | 9.0 |
|  | 500 | 9.0 |
|  | 250 | 9.0 |
|  | 100 | 9.0 |
|  | 50 | 9.0 |
|  | 25 | 8.5 |
|  | 10 | 8.5 |
| $N^1$-Perfluoroctanoyl-3'-nitro-5'-trifluoromethyl-o-phenylenediamine | 1000 | 9.0 |
|  | 500 | 9.0 |
|  | 250 | 9.0 |
|  | 100 | 9.0 |
|  | 50 | 9.0 |
|  | 25 | 9.0 |

Results essentially the same as those reported in Examples 86–119 are obtained when evaluating in the same procedures the following compounds:

$N^1,N^2$-Bis(2,2-difluorobutyryl)-3'-nitro-5'-trifluoromethyl-o-phenylenediamine $N^1,N^2$-Bis(2,2-difluoro-4-bromobutyryl)-3'-nitro-5'-trifluoromethyl-o-phenylenediamine $N^1$-(2,2-Difluoro-3-bromopropionyl)-$N^2$-(2-chloro-4-tert-butylbenzoyl)-3'-nitro-5'-trifluoromethyl-o-phenylenediamine $N^1$-Difluorochloroacetyl-$N^2$-(phenoxycarbonyl)-3'-nitro-5'-difluoromethyl-o-phenylenediamine $N^1$-Naphthoyl-$N^2$-trifluoroacetyl-3'-nitro-5'-trifluoromethyl-o-phenylenediamine $N^1,N^2$-Bis(difluoroacetyl)-3'-nitro-5'-difluoromethyl-o-phenylenediamine $N^1$-Trifluoroacetyl-$N^2$-(p-n-butoxybenzoyl)-4'-trifluoromethyl-6'-nitro-o-phenylenediamine $N^1$-Trifluoroacetyl-$N^2$-(p-nitrobenzoyl)-4'-trifluoromethyl-6'-nitro-o-phenylenediamine $N^1$-Pentafluoropropionyl-$N^2$-(2,2-dichloropropionyl)-4'-trifluoromethyl-6'-nitro-o-phenylenediamine $N^1$-Trifluoroacetyl-$N^2$-(2,2-dichloropropionyl)-4'-trifluoromethyl-6'-nitro-o-phenylenediamine $N^1$-Heptafluorobutyryl-3'-nitro-5'-trifluoromethyl-o-phenylenediamine $N^1$-Trifluoroacetyl-$N^2$-pentafluoropropionyl-4'-trifluoromethyl-6'-nitro-o-phenylenediamine $N^1$-Pentafluoropropionyl-3'-nitro-5'-trifluoromethyl-o-phenylenediamine $N^1$-Trifluoroacetyl-$N^2$-dichlorofluoroacetyl-4'-trifluoromethyl-6'-nitro-o-phenylenediamine $N^1$-Trifluoroacetyl-$N^2$-methoxycarbonyl-4'-trifluoromethyl-6'-nitro-o-phenylenediamine $N^1$-Pentafluoropropionyl-$N^2$-trichloroacetyl-3'-nitro-5'-trifluoromethyl-o-phenylenediamine $N^1$-Difluorochloroacetyl-$N^2$-propionyl-4'-trifluoromethyl-6'-nitro-o-phenylenediamine $N^1$-Pentadecafluorooctanoyl-3'-nitro-5'-trifluoromethyl-o-phenylenediamine $N^1$-Trifluoroacetyl-$N^2$-trichloroacetyl-4'-trifluoromethyl-6'-nitro-o-phenylenediamine In addition to herbicidal and insecticidal activity, compounds of the present invention exhibit anthelmintic, anti-inflammatory, and nematocidal activity.

The anthelmintic and anti-inflammatory activity is most pronounced among compounds of Formula II. The nematocidal activity is exhibited by compounds representative of the entire scope of the present invention.

In respect to the anthelmintic activity, the compounds of Formula II can be administered to warm-blooded animals for the control of internal parasites, particularly parasites of the intestinal tract such as *Haemonchus contortus, Syphacia obvelata, Nematospiroides dubius*, and the like. Administration is conveniently by the oral route, and may take the form of inclusion in a diet, or of separate administration of the subject compound alone or formulated as a tablet, bolus, etc. for administration. Typically, good results are obtained at dosages of from 5 to 500 mg./kg. for single doses, and at dosages of from 0.001 to 0.05 percent in the diet. In representative procedures, N'-trifluoroacetyl-3'-nitro-5'-trifluoromethyl-o-phenylenediamine was incorporat in a modified mouse diet in a concentration of 0.01 percent. The modified diet was fed to a group of four mice; an unmodified diet was fed to another group of four mice to serve as a control. The mice of both groups were infected with *Nematospiroides dubius* about seven hours after initiation of feeding. Feeding was continued for eight days; on the ninth day, all mice were necropsied and the upper intestines examined to ascertain the presence, and if present numbers, of *Nematospiroides dubius*. In the group of mice on the modified diet, no larvae were seen; in the control group, an average of 28 larvae per mouse were seen. Like results are obtained with other of the compounds of Formula II.

The compounds of Formula II are also useful as anti-inflammatory agents in warm-blooded animals. Oral administration is most convenient and is therefore preferred. However, the compounds can be formulated to facilitate such administration. Thus, the compounds can be formulated in liquid or solid formulations, such as tablets, pills, capsules, granules, powders, oral solutions or suspensions, and the like. The exact concentration of the active agent in such formulation is not critical, it being necessary only that an appropriate dosage of the active agent be supplied to the animal being treated. In general, an anti-inflammatory effect is achieved at rates of from 1 to 100 milligrams, or more, per kilogram of animal body weight, depending upon the particular compound chosen, mode of application and the like. Such dosage can be administered at one time, or in several administrations over a given period of time, such as daily.

The compounds of the present invention can be used for the control of diseases caused by fungal and nematode organisms such as root-know nematode, stem nematode, fusarium root-rot, and Rhizoctonia. In general, control is achieved at rates of from 1 to 40 pounds per acre. In standardized testing procedures, the following compounds were found to give complete or essentially complete control of root-knot nematode at the designated application rate:

$N^1$-trifluoroacetyl-3',4',5',6'-tetrachloro-o-phenylenediamine (5 pounds per acre)

$N^1$-trifluoroacetyl-$N^2$-naphthoyl-4'-trifluoromethyl-6'-nitro-o-phenylenediamine (20 pounds per acre)

$N^1$-trifluoroacetyl-$N^2$-(3,4-dichlorobenzoyl)-4'-trifluoromethyl-6'-nitro-o-phenylenediamine (20 pounds per acre).

As discussed hereinabove, the novel compounds of the present invention can be employed as herbicides in a wide variety of embodiments. In all such embodiments, the described compounds can be formulated and employed with known herbicides of other classes. The ratio of the individual components of such compositions to one another is not critical; all ratios provide compositions that have useful plant growth altering properties. However, generally preferred compositions are those wherein a substantial portion of each component is present — such as compositions wherein the ratio of the components ranges from 1:10 to 10:1, and especially from 1:5 to 5:1.

Known herbicides with which the compounds of the present invention are preferably combined include:
N,N-di-n-propyl-2,6-dinitro-4-(trifluoromethyl)aniline,
N,N-di-n-propyl-2,6-dinitro-4-methylaniline,
N-ethyl-N-butyl-2,6-dinitro-4-(trifluoromethyl)aniline,
N,N-di-n-propyl-2,6-dinitro-4-(methylsulfonyl)aniline,
N,N-di-n-propyl-2,6-dinitro-4-sulfamoylaniline,
N,N-di-n-propyl-2,6-dinitro-4-isopropylaniline,
N,N-di-n-propyl-2,6-dinitro-4-tert-butylaniline, and
N,N-bis(2-chloroethyl)-2,6-dinitro-4-methylaniline.

These combinations are exemplified by the following example.

EXAMPLE 120

The combination of $N^1$-(pentafluoropropionyl)-3'-nitro-5'-(trifluoromethyl)-o-phenylenediamine and N,N-di-n-propyl-2,6-dinitro-4-(trifluoromethyl)aniline was evaluated for preemergent application, employing various species of plants.

A soil was prepared consisting of one part masonry sand and one part shredded top soil blended together in a cement mixer. One gallon of this soil was then placed in a 21.5 × 31.5 cm. galvanized flat and was patted down with a bench brush until level. Rows were marked, and seeds planted, one species to a row, except that in the case of the mixture, the mixture was likewise seeded in one row. The species employed were cotton (two separate rows), morning glory (*Ipomea purpurea*), foxtail millet, jimsonweed, velvetleaf, and a mixture of sickle pod, pigweed, cypressvine morning glory (*Ipomea quamoclit*), and Crotolaria.

A treated cover soil was then prepared. The compounds were separately formulated by suspending each in a 1:1 solution of acetone and ethanol containing a small amount of a blend of two sulfonate-nonionic surfactants. Each suspension was then further diluted serially with an aqueous solution of the same blend of surfactants — to prepare a plurality of aqueous treating solutions containing the respective compounds in various concentrations, in addition to the blend of surfactants uniformly in a total concentration of 0.55 percent, and the acetone and ethanol uniformly each in a concentration of 4.15 percent. Treating solution containing each of the compounds were sprayed onto a portion of soil of the same type as described above, while rotating in a cement mixer. The rotation was continued for 5–7 minutes. Each portion of soil so treated was then spread over a flat to a depth of three-eighths inch.

Another flat was prepared and seeded in like manner, except that the cover soil was left untreated to serve as a control. All flats were held for thirteen days under normal greenhouse conditions, at which time injury ratings and observations as to type of injury were made. The injury rating scale used was as follows:

0—no injury
1–3—slight injury
4–6—moderate injury
7–9—severe injury
10—death
B—burned
N—no germination
R—reduced germination
S—stunting The following table reports the results of the evaluation of the treated flats. In the control flats, there were healthy stands of each of the test species.

TABLE II

| Compounds and Rates in Pounds/Acre | Cotton | Morning Glory | Foxtail Millet | Jimsonweed | Cotton | Mixture | Velvetleaf |
|---|---|---|---|---|---|---|---|
| A, ¼ lb.; B, ⅛ lb. | 0 | 2B | 10N | 0 | 0 | 8RS | 0 |
| A, ½ lb.; B, ⅛ lb. | 0 | 2B | 9RS | 0 | 0 | 7RS | 0 |
| A, 1 lb.; B, ⅛ lb. | 2S | 9BRS | 10N | 8BS | 0 | 4RS | 0 |
| A, 2 lbs.; B, ⅛ lb. | 3RS | 10N | 10N | 9.5BRS | 4BS | 8RS | 2S |
| A, ¼ lb.; B ¼ lb. | 0 | 2BS | 10N | 2S | 2BS | 9.5RS | 3S |
| A, ½ lb.; B, ¼ lb. | 0 | 6BS | 10N | 4BS | 2S | 8BRS | 0 |
| A, 1 b.; B, ¼ lb. | 0 | 5BS | 10N | 9BRS | 0 | 10N | 0 |
| A, 2 lbs.; B, ¼ lb. | 0 | 10N | 10N | 8BS | 3S | 9RS | 4S |

A = N¹-(pentafluoropropionyl)-3'-nitro-5'-(trifluoromethyl)-o-phenylenediamine
B = N,N-di-n-propyl-2,6-dinitro-4-(trifluoromethyl)aniline Like results are achieved when combining N¹-(pentafluoropropionyl)-3'-nitro-5'-(trifluoromethyl)-o-phenylenediamine or other of the novel compounds of the present invention with other of the dinitroaniline compounds identified hereinabove. In general, good results are obtained when the combinations are employed to supply from 0.5 to 8.0 pounds of the N-(2,2-difluoroalkanoyl)-o-phenylenediamine per acre, and from 0.25 to 2.50 pounds of the dinitroaniline per acre.

The starting materials to be employed in accordance with the present invention are prepared in known procedures, and some of them are commercially available. Those starting materials which are of the formula

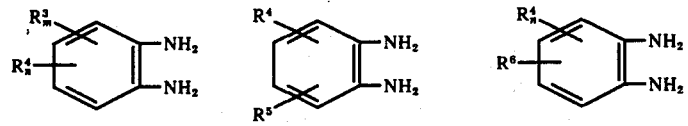

are prepared by a plurality of synthetic steps as are necessary to introduce the required moieties. Most conveniently, one or both of the NH₂ groups are introduced by conversion of a halo group. Also, the amino group or groups can be introduced by nitration and subsequent reduction. These various synthetic steps are generally and most conveniently carried out with starting materials already bearing the requisite R³, R⁴, R⁵ and R⁶ moieties. However, it is sometimes preferred that these substituents, where, e.g., nitro or halo, be introduced simultaneously with the synthetic steps leading to the introduction of the amino groups.

Thus, for example, where the diamine is tetrasubstituted, the corresponding tetrasubstituted benzene is nitrated at each of the remaining ortho positions and the nitro groups then reduced. A 3-nitro-5-substituted diamine where the substituent is cyano or loweralkylsulfonyl is readily prepared by nitrating a 5-substituted-2-hydroxynitrobenzene to introduce a 3-nitro group, followed by conversion of the hydroxy group to a chloro, amination, and selective reduction.

Those of the compounds of the present invention wherein R¹ is a moiety other than hydrogen or the same acyl moiety as R are generally prepared from diamine starting materials already bearing the requisite R¹ moiety. These starting materials are themselves prepared from the corresponding diamine starting materials described above, by reaction with an appropriate acyl halide or, in the instance of R¹ or R² representing

with an appropriate loweralkyl or phenyl haloformate. Alternately, however, these starting materials can be prepared from o-nitroanilines:

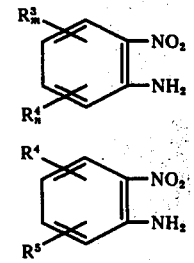

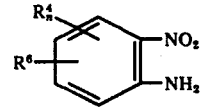

by acylation and subsequent reduction, both in procedures well known in the prior art.

In an additional embodiment of the present invention, $N^1$-(2,2,3,3-tetrafluoropropionyl)-3'-nitro-5'-trifluoromethyl-o-phenylenediamine was evaluated in the procedures of Examples 28–31 and also in the procedures of Examples 32–35. The results were as reported below

TABLE XII

| | Injury Rating on Preemergent Treatment | | | | | | |
|---|---|---|---|---|---|---|---|
| Lbs./Acre | Corn | Cotton | Soybean | Crabgrass | Pigweed | Foxtail | Velvetleaf |
| 8 | 1 | — | — | 3 | 4 | 3 | 4 |
| 4 | 0 | 1 | 1 | 2 | 4 | 3 | 4 |
| 2 | 0 | 0 | 0 | 3 | 4 | 3 | 4 |
| 1 | 0 | 1 | 0 | 2 | 3 | 2 | 3 |

TABLE XIII

| | Injury Rating on Postemergent Treatment | | | |
|---|---|---|---|---|
| Lbs./Acre | Corn | Crabgrass | Pigweed | Foxtail | Velvetleaf |
| 8 | 2 | 4 | 4 | 4 | 4 |
| 4 | 3 | 4 | 4 | 4 | 4 |
| 2 | 3 | 4 | 4 | 4 | 3 |
| 1 | 1 | 4 | 4 | 4 | 4 |

I claim:

1. The method for the control of insect and arachnid pests which comprises contacting an insect or arachnid with an inactivating amount of an active agent, said active agent being a compound of the formula

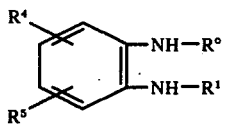

wherein
$R°$ represents a 2,2-difluoroalkanoyl radical of the formula

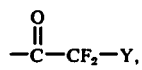

wherein Y represents hydrogen, chlorine, fluorine, difluoromethyl, perfluoroalkyl of $C_1$–$C_6$, or radical of the formula

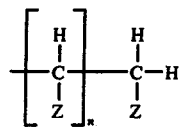

wherein each Z independently represents hydrogen or halogen and $n$ represents 0 or 1;
$R^1$ represents
hydrogen,
radical of the formula $$-\overset{O}{\underset{\|}{C}}-O-Y^1,$$

wherein $Y^1$ represents loweralkyl of $C_1$–$C_4$ or phenyl,
benzoyl,
furoyl,
naphthoyl, or
substituted benzoyl of the formula

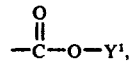

wherein each $Z'$ independently represents halo or nitro, $Z''$ represents loweralkyl of $C_1$–$C_4$ or loweralkoxy of $C_1$–$C_4$, $p$ represents 0, 1, or 2, $q$ represents 0 or 1, and the sum of $p$ and $q$ is 1–3;
$R^4$ represents nitro; and
$R^5$ represents trifluoromethyl, difluoromethyl, or difluorochloromethyl, subject to the limitations (1) that $R^4$ and $R^5$ are meta to one another, and (2) that where $R^1$ represents hydrogen, the ring position ortho to the —NH-$R^1$ bears one of the designated $R^4$ or $R^5$ moieties.

2. The method of claim 1 wherein the active agent is $N^1$-trifluoroacetyl-3'-nitro-5'-trifluoromethyl-o-phenylenediamine.

3. The method of claim 1 wherein the active agent is $N^1$-difluorochloroacetyl-3'-nitro-5'-trifluoromethyl-o-phenylenediamine.

* * * * *